(12) United States Patent
Cho et al.

(10) Patent No.: US 12,285,399 B2
(45) Date of Patent: Apr. 29, 2025

(54) COMPOSITION COMPRISING BORNYL ACETATE OR PHARMACEUTICALLY ACCEPTABLE SALT THEREOF AS ACTIVE INGREDIENT FOR PREVENTION OR TREATMENT OF STRESS-RELATED DISORDER

(71) Applicant: UNIVERSITY-INDUSTRY COOPERATION GROUP OF KYUNG HEE UNIVERSITY, Yongin-si (KR)

(72) Inventors: Ik-Hyun Cho, Seoul (KR); Jong-Hee Choi, Gyeongju-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 792 days.

(21) Appl. No.: 17/439,578

(22) PCT Filed: Mar. 18, 2020

(86) PCT No.: PCT/KR2020/003695
§ 371 (c)(1),
(2) Date: Sep. 15, 2021

(87) PCT Pub. No.: WO2020/190024
PCT Pub. Date: Sep. 24, 2020

(65) Prior Publication Data
US 2022/0151971 A1   May 19, 2022

(30) Foreign Application Priority Data
Mar. 18, 2019   (KR) .................. 10-2019-0030527

(51) Int. Cl.
*A61K 31/215*   (2006.01)
*A23L 33/10*   (2016.01)
*A61P 25/00*   (2006.01)

(52) U.S. Cl.
CPC ............ *A61K 31/215* (2013.01); *A61P 25/00* (2018.01)

(58) Field of Classification Search
CPC ....... A61K 31/215; A61P 25/00; A23L 33/10; A23V 2002/00; A23V 2200/31; A23V 2200/322; A23V 2250/30
See application file for complete search history.

(56) References Cited

FOREIGN PATENT DOCUMENTS

| | | |
|---|---|---|
| JP | 2009-235015 A | 10/2009 |
| JP | 2012-171944 A | 9/2012 |
| KR | 10-2017-0066851 A | 6/2017 |

OTHER PUBLICATIONS

JP2009235015—machine-translation, machine translation of JP2009235015, 2024.*
Alzheimers Disease Prevention, 2024, https://www.nhs.uk/conditions/alzheimers-disease/prevention/#:~:text=As%20the%20exact%20cause%20of,way%20to%20prevent%20the%20condition.*
Bong Han Lee et al., "Antioxidative and Neuroprotective Effects of Volatile Components in Essential Oils from Chrysanthemum indicum Linne Flowers", Food Sci. Biotechnol, Apr. 30, 2015, pp. 717-723, vol. 24, No. 2.
Eri Matsubara et al., "(-)-Bornyl acetate induces autonomic relaxation and reduces arousal level after visual display terminal work without any influences of task performance in low-dose condition", Biomedical Research, 2011, pp. 151-157, vol. 32, No. 2.
International Search Report for PCT/KR2020/003695, dated Sep. 1, 2020.

* cited by examiner

*Primary Examiner* — Sun Jae Yoo
(74) *Attorney, Agent, or Firm* — Sughrue Mion, PLLC

(57) ABSTRACT

When used as an active ingredient, bornyl acetate or a pharmaceutically acceptable salt thereof according to the present invention exhibits the effects of alleviating behavioral scales in an animal model, inhibiting the activation of microglia and the generation of inflammatory factors (COX-2 and iNOS), and lowering nerve excitability for responsiveness to cell-neural stimuli. Thus, bornyl acetate or a pharmaceutically acceptable salt thereof is found to have an excellent stress modulating potential and to be useful for the prevention and treatment of stress-related diseases, especially, depression, thereby finding advantageous applications in related industries.

5 Claims, 9 Drawing Sheets
Specification includes a Sequence Listing.

COMPOSITION COMPRISING BORNYL ACETATE OR PHARMACEUTICALLY ACCEPTABLE SALT THEREOF AS ACTIVE INGREDIENT FOR PREVENTION OR TREATMENT OF STRESS-RELATED DISORDER

CROSS-REFERENCE TO RELATED APPLICATIONS

This application is a National Stage of International Application No. PCT/KR2020/003695 filed Mar. 18, 2020, which claims priority based on Korean Patent Application No. 10-2019-0030527 filed on Mar. 18, 2019, the entire disclosures of which are incorporated herein by reference.

TECHNICAL FIELD

The present invention relates to a composition for preventing or treating stress-related diseases, the composition including bornyl acetate or a pharmaceutically acceptable salt thereof as an active ingredient.

BACKGROUND ART

When a human is physically or psychologically stressed due to stimuli from internal and external environments, the human body releases locus ceruleus norepinephrine (LC-NE) and corticotropin releasing hormone (CRH) in the brain to adapt to the stress. LC-NE activates the sympathetic nervous system and inhibits the action of the parasympathetic nervous system to increase blood pressure, heart rate, and respiration, thereby expanding the bronchi, as well as increases sweating, which causes goosebumps on the skin. CRH secreted by the hypothalamus releases adrenocorticotropic hormone (ACTH) from the anterior pituitary in the general systemic circulation. This ACTH moves along the blood and binds to the ACTH receptor in the adrenal cortex to synthesize a secondary signal messenger called cAMP. Protein kinase A (PKA) activated by cAMP activates a glucocorticoid synthesis protein located in the mitochondria. The glucocorticoid synthesis protein then uses cholesterol so as to generate stress hormones. Representative examples of glucocorticoids include cortisol, corticosterone, cortisone, and the like. The stress pathway leading to the CRH-ACTH-glucocorticoid is commonly referred to as the hypothalamus-pituitary gland-adrenal gland (HPA) axis. Glucocorticoids regulate carbohydrate metabolism in the liver, such as gluconeogenesis, glycogen storage, and blood sugar level elevation. In addition, glucocorticoids act as an anti-inflammatory by suppressing the expression of various immune substance-producing genes in immune cells responsible for immunity. Further, when this hormone content in the blood increases, it acts on the pituitary gland as negative feedback to inhibit ACTH secretion.

A body-acceptable level of stress acts as an appropriate stimulant for the human body, but strong and persistent psychological and physical stress outside the allowable range induces excessive secretion of glucocorticoids for a long time. Glucocorticoids secreted in excess for a long time weaken the body's immunity to reduce resistance to external infections and induce various diseases in our body. In addition to weakening immunity, it specifically causes brain cell damage and inhibits brain regeneration, inducing insomnia, lethargy, hypomnesia, depression, and even suicidal thoughts.

Starting with tricyclic drugs developed in the 1960 s as a treatment for depression, various types of antidepressant drugs such as Prozac, Zoloft, Seroxat, Efexor, and Remeron, which are currently known as serotonin reuptake inhibitors, have been developed. In addition to such antidepressant drugs, many studies have been conducted to develop CRH receptor inhibitors that bind to CRH, which is the primary substance of the stress response, but side effects are reported.

Accordingly, the present inventors have found that bornyl acetate or a pharmaceutically acceptable salt thereof as an active ingredient is used to improve the behavioral scale of animal models and to inhibit the activation of microglia and the generation of inflammatory factors (COX-2 and iNOS) as well as an effect of lowering the degree of nerve excitability for responsiveness to cell-neural stimulation so that it has excellent stress control ability and is useful for preventing and treating stress-related diseases, particularly depression, thereby completing the present invention.

DISCLOSURE

Technical Problem

An object of the present invention is to provide a pharmaceutical composition for preventing or treating stress-related diseases, the composition including bornyl acetate or a pharmaceutically acceptable salt thereof as an active ingredient.

Another object of the present invention is to provide a food composition for preventing or alleviating stress-related diseases, the composition including bornyl acetate or a pharmaceutically acceptable salt thereof as an active ingredient.

Still another object of the present invention is to provide a method for preventing and treating stress-related diseases, the method including administering to an individual a pharmaceutically effective amount of the pharmaceutical composition.

Technical Solution

In order to achieve the above object, the present invention provides a pharmaceutical composition for preventing or treating stress-related diseases, the composition including bornyl acetate or a pharmaceutically acceptable salt thereof as an active ingredient.

Further, the present invention provides a food composition for preventing or alleviating stress-related diseases, the composition including bornyl acetate or a pharmaceutically acceptable salt thereof as an active ingredient.

Further, the present invention provides a method for preventing and treating stress-related diseases, the method including administering to an individual a pharmaceutically effective amount of the pharmaceutical composition.

Advantageous Effects

The bornyl acetate or a pharmaceutically acceptable salt thereof of the present invention as an active ingredient is used to improve the behavioral scale of an animal model, to inhibit the activation of microglia and the generation of inflammatory factors (COX-2 and iNOS) and to have an effect of lowering the degree of nerve excitability for responsiveness for cell-neural stimulation so that it has excellent stress control ability and is thus useful in preventing and treating stress-related diseases, in particular, depression, and thus usefully applied to related industries.

BEST MODES OF THE INVENTION

Figure 1A:
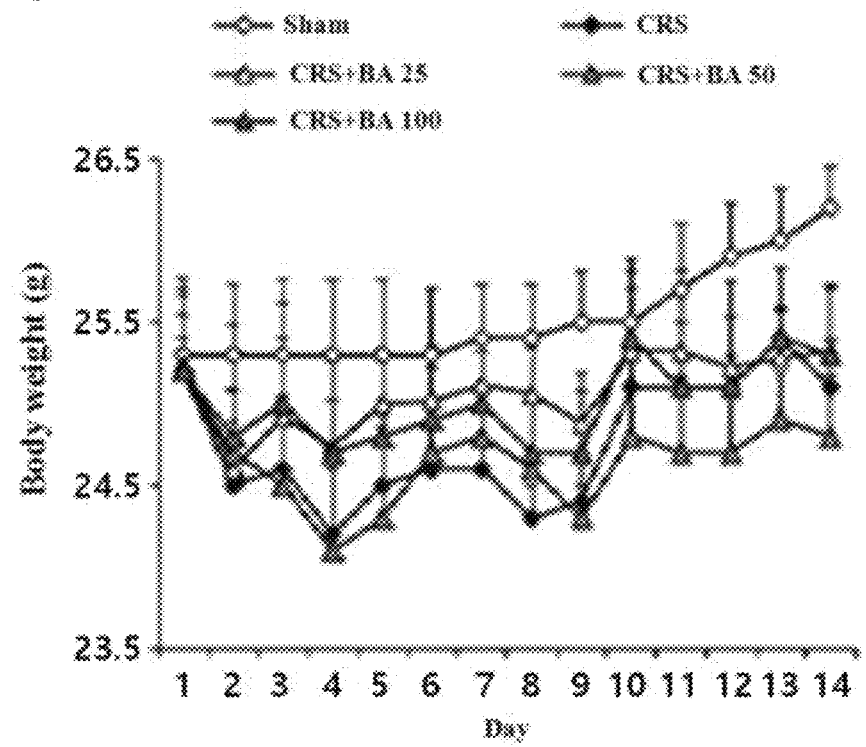
FIG. 1A is a view confirming body weight in an animal model of stress depression induced by chronic restrained stress (CRS).

The present invention provides a pharmaceutical composition for preventing or treating stress-related diseases, the composition including bornyl acetate or a pharmaceutically acceptable salt thereof as an active ingredient.

The term "preventing" used in the present invention refers to any action that inhibits or delays a stress-related disease by administration of the pharmaceutical composition. In addition, the term "treating" refers to any action that improves or beneficially changes the symptoms of stress-related diseases by administration of the pharmaceutical composition.

The bornyl acetate may be represented by Formula 1 below. The bornyl acetate may include a derivative thereof and may further include a pharmaceutically acceptable salt thereof.

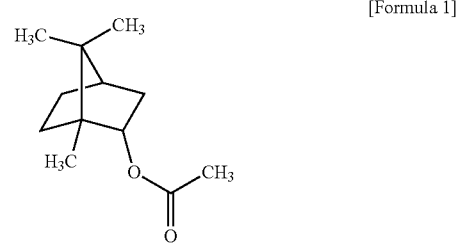

[Formula 1]

The stress disease is selected from the group consisting of depression, anxiety, fatigue syndrome, neurodegenerative disease, eating disorder, anorexia nervosa, drug addiction, drug and alcohol withdrawal syndrome and stressful psychotic episode, preferably depression, but is not limited thereto.

The bornyl acetate of the present invention as an active ingredient is used to confirm that the behavioral scale is improved through the bodyweight change, tail suspension test, forced swimming test, and serum stress hormone (corticosterone) level change in an animal model of stress depression induced by chronic restrained stress (CRS). Further, while the activation of microglia is inhibited, and the generation of inflammatory factors (COX-2 and iNOS) is inhibited, it has an effect of lowering the degree of excitability of the visual field for responsiveness for cell-neural stimulation so that it has excellent stress control ability and is thus useful in preventing and treating stress-related diseases, in particular, depression.

As the salt, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, non-toxic organic acids such as aliphatic mono/dicarboxylate, phenyl-substituted alkanoate, hydroxy alkanoate, alkandioate, aromatic acids and aliphatic/aromatic sulfonic acids, or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts include sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, hydroxybutyrate, glycolate, malate, tartrate, methanesulfonate, propanesulfonate, naphthalene-1-sulfonate, naphthalene-2-sulfonate or mandelate.

The pharmaceutical composition according to the present invention may be prepared in a form in which the active ingredient is incorporated into a pharmaceutically acceptable carrier. In this case, the pharmaceutically acceptable carrier includes carriers, excipients and diluents commonly used in the pharmaceutical field. Pharmaceutically acceptable carriers that can be used in the pharmaceutical composition of the present invention may include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, methylhydroxybenzoate, propylhydroxybenzoate, talc, magnesium stearate and mineral oil.

The pharmaceutical composition of the present invention may be formulated in the form of the oral formation such as powders, granules, tablets, capsules, suspensions, emulsions, syrups, aerosols, etc., external preparations, suppositories, or sterile injection solutions according to conventional methods, respectively.

In the case of formulation, it may be prepared using diluents or excipients such as fillers, extenders, binders, wetting agents, disintegrants, surfactants, etc., commonly used. Solid preparations for oral administration include tablets, pills, powders, granules, capsules, etc., and such solid preparations include at least one excipient, for example, starch, calcium carbonate, sucrose, lactose, and gelatin in the active ingredient. In addition to simple excipients, lubricants such as magnesium stearate and talc may also be used. Liquid formulations for oral administration include suspensions, internal solutions, emulsions, syrups, etc. In addition to water and liquid paraffin, which are commonly used diluents, various excipients such as wetting agents, sweeteners, fragrances, and preservatives are included. Formulations for parenteral administration include sterile aqueous solutions, non-aqueous solutions, suspensions, emulsions, lyophilized formulations and suppositories. As the non-aqueous solvent and suspending agent, propylene glycol, polyethylene glycol, vegetable oils such as olive oil, and injectable esters such as ethyl oleate may be used. As a base of the suppository, witepsol, tween 61, cacao butter, laurin, glycerol gelatin, etc. may be used.

The pharmaceutical composition according to the present invention may be administered to an individual by various routes. Any mode of administration can be applied, for example, by oral, intravenous, intramuscular, subcutaneous, intraperitoneal injection.

The dosage of the pharmaceutical composition according to the present invention is selected in consideration of the individual's age, weight, gender, physical condition, and the like. It is apparent that the concentration of the active ingredient included in the pharmaceutical composition may be variously selected depending on the subject, and is preferably included in the pharmaceutical composition at a concentration of 0.01 to 5,000 µg/ml. If the concentration is less than 0.01 µg/ml, pharmaceutical activity may not appear, and if it exceeds 5,000 µg/ml, it may be toxic to the human body.

Further, the present invention provides a food composition for preventing or alleviating stress-related diseases, the composition including bornyl acetate or a pharmaceutically acceptable salt thereof as an active ingredient.

The food composition of the present invention may include various flavoring agents or natural carbohydrates as additional ingredients like a conventional food composition in addition to including the extract as an active ingredient.

Examples of the above-mentioned natural carbohydrates include monosaccharides such as glucose, and fructose; disaccharides such as maltose, and sucrose; and polysaccharides such as conventional sugars such as dextrin and cyclodextrin, and sugar alcohols such as xylitol, sorbitol, and erythritol. The above-mentioned flavoring agents may advantageously use natural flavoring agents (thaumatin), stevia extracts (for example, rebaudioside A, glycyrrhizin, etc.) and synthetic flavoring agents (saccharin, aspartame, etc.). The food composition of the present invention may be formulated in the same manner as the pharmaceutical composition and used as a functional food or added to various foods. Foods to which the composition of the present invention can be added include, for example, beverages, meat, chocolate, foods, confectionery, pizza, ramen, other noodles, gums, candy, ice cream, alcoholic beverages, vitamin complexes and health supplements.

In addition, the food composition may include various nutrients, vitamins, minerals (electrolytes), flavoring agents such as synthetic flavoring agents and natural flavoring agents, colorants, thickeners (cheese, chocolate, etc.), pectic acid and its salts, alginic acid and its salts, organic acids, protective colloidal thickeners, pH adjusters, stabilizers, preservatives, glycerin, alcohols, carbonation agents used in carbonated beverages, and the like. In addition, the food composition of the present invention may include natural fruit juice and pulp for the production of fruit juice beverages and vegetable beverages.

The functional food composition of the present invention may be manufactured and processed in the form of tablets, capsules, powders, granules, liquids, pills, and the like. In the present invention, the term 'health functional food composition' refers to a food manufactured and processed using raw materials or ingredients with functions useful for the human body according to Act No. 6727 of the Health Functional Food Act and refers to ingestion for the purpose of obtaining useful effects for health purposes such as regulating nutrients or physiological effects for the structure and function of the human body. The health functional food of the present invention may include conventional food additives. Unless otherwise specified, whether it is suitable as a food additive is determined according to the criteria and standards related to the item according to the general rules and general test method of the Korea Food Additives Code approved by the Ministry of Food and Drug Safety. The items listed in the "Food Additives Code" include, for example, chemical compounds such as ketones, glycine, calcium citrate, nicotinic acid, and cinnamic acid; natural additives such as persimmon pigment, licorice extract, crystalline cellulose, kaoliang color, and guar gum; mixed preparations such as a sodium L-glutamate preparation, an alkali additive for noodles, a preservative preparation, and a tar dye preparation, etc. For example, the health functional food in the form of tablets is prepared such that the active ingredient of the present invention is mixed with excipients, binders, disintegrants and other additives, the mixture is granulated by a conventional method followed by compression molding with a lubricant, etc. or the mixture may be compression molded directly. In addition, the health functional food in the form of tablets may contain a flavoring agent or the like, if necessary. Among health functional foods in the form of capsules, hard capsules may be prepared by filling a mixture of the active ingredient of the present invention with additives such as excipients in conventional hard capsules. Soft capsules may be prepared by filling a mixture of the active ingredient of the present invention with additives such as excipients in a capsule base such as gelatin. The soft capsules may include plasticizers such as glycerin or sorbitol, colorants, a preservative, and the like, if necessary. The health functional food in the form of pills may be prepared by molding a mixture of the active ingredient of the present invention with excipients, binders, disintegrants, etc., by a known method. If necessary, it may be coated with sucrose or other coating agents. Further, the surface may be coated with a material such as starch or talc. The health functional food in the form of granules may be prepared in granular form by mixing a mixture of the active ingredient of the present invention with excipients, binders, disintegrants, etc., by a conventionally known method. It may include fragrance ingredients, flavoring agents, etc., if necessary.

Further, the present invention provides a method for preventing and treating stress-related diseases, the method including administering to an individual a pharmaceutically effective amount of the pharmaceutical composition.

The pharmaceutical composition of the present invention is administered in a therapeutically effective amount or in a pharmaceutically effective amount. The term "pharmaceutically effective amount" means an amount sufficient to treat a disease with a reasonable benefit/risk ratio applicable to medical treatment, and the effective dose level may be determined according to factors including the subject type, severity, age, gender, the activity of the drug, sensitivity of the drug, administration time, administration route, excretion rate, duration of treatment, concurrent drugs, and other factors well known in the medical field.

MODES OF THE INVENTION

The present invention is described in more detail through the following Examples. However, the following Examples are only for specifying the contents of the present invention, but the present invention is not limited thereto.

Preparation Example 1

1-1. Classification of Experimental Groups

In order to confirm the antidepressant effect of the bornyl acetate (BA) of the present invention on an animal model of depression, they were divided into the following experimental groups.

Sham group: Normal control group in which chronic restrained stress (CRS) was not induced, and bornyl acetate was not administered CRS group: Group in which CRS was induced, and PBS was administered orally CRS+BA group: Group in which CRS was induced, and bornyl acetate was administered (25, 50 and 100 mg/kg)

BA group: Group in which CRS was not induced, and bornyl acetate was administered (100 mg/kg) orally 1-2. Induction of Stress Depression Animal Model In order to confirm the antidepressant efficacy of bornyl acetate on the animal model of stress depression, an animal model of depression induced by chronic restrained stress (CRS) was prepared. Specifically, the animal model, 8-week-old male C57BL/6NTac mice after birth (Narabiotechnology, Korea; weight 22-24 g) had been stabilized for 1 week. A 50 ml conical tube (SPL Life sciences, Pocheon, Korea) was punched to make a hole, thereby making a restraint frame. The mice were put in the frame and restrained for 2 hours every day for 14 days. After restraint, the mice were allowed to freely ingest water and food in the home cage.

1-3. Behavioral Experiment

1) Tail Suspension Test (TST)

On the 14th day after chronic restrained stress was induced, the tail tip of the mouse was fixed and hanged upside down on a horizontal bar (1 cm in diameter) installed at a height of about 50 cm from the floor, and then the time of immobility was measured. Measurements were made during the last 4 minutes of the 6-minute test period.

2) Forced Swimming Test (FST)

24 hours after the tail suspension test, distilled water (23-24° C.) was filled to a height of about 14 cm in a circular water tank (diameter 15×height 25 cm), and the mice were dropped and forced to swim. The time of immobility (which means a case in which three legs of a mouse do not move with minimal movement or mice float using one of the hind paws) during the last 4 minutes of the total 6-minute test period was measured.

1-4. Administration of Bornyl Acetate

Bornyl acetate (25, 50 and 100 mg/kg) of the present invention was dissolved in 0.1 M PBS, and the mixture was orally administered 1 hour before inducing restrained stress every day. Bornyl acetate was administered in a dose per individual of 100 μl.

1-5. Enzyme-Linked Immunosorbent Assay

Bornyl acetate (25, 50 and 100 mg/kg) was orally administered 1 hour before inducing restrained stress every day. 14 days later, the mice were anesthetized, and the blood was collected. The blood was centrifuged at 5,000 rpm for 15 minutes to separate serum. In order to confirm the level of corticosterone, a stress hormone, in serum, an enzyme-linked immunosorbent assay (ELISA) kit (Enzo life sciences, Farmingdale, NY, USA) was used for analysis.

1-6. Immunohistochemistry Staining

Bornyl acetate (100 mg/kg) was administered orally 1 hour before induction of restraint stress every day. 14 days later, the mice were anesthetized, and 4% paraformaldehyde was perfused into the heart. Then, the mice were fixed, and the brain was excised. The excised brain was immersed in 4% paraformaldehyde and fixed at 4° C. for one more day. It was then changed to 30% sucrose, and the brain was stored at 4° C. for 3 days or more to prevent freeze damage. The brain was cut into a thickness of 30 μm using a cryocut microtome to prepare the frozen sections. For immunohistochemistry staining, the sections were treated with a blocking solution [200 μg of bovin serum albumin (BSA, Sigma, USA), 500 μl of fetal bovine serum (FBS, Gibco, Germany), 500 μl of normal goat serum (NGS, Vector Laboratories, USA) and 10 μl of Triton X-100 (Sigma, USA) were put in phosphate-buffered saline (PBS) to make 10 μl] and reacted for 1 hour. Then, it was washed with PBS, and it was replaced with a solution in which the primary antibody [Iba-1 (a marker of microglia) and c-Fos (a marker of cell excitability) was diluted in a blocking solution. Then they were reacted for 12 hours or more. Then, after washing with PBS, it was replaced with a solution in which the secondary antibody was diluted in PBS at a ratio of 1:200. Then, they were reacted for 1 hour, and then washed with PBS. Then, immunostaining was performed using an avidin-biotin-peroxidase complex (1:200; Vector Laboratories, USA) and 3,3'-diamino-benzidine.

1-7. Western Blot Analysis

The hippocampus and amygdala of the brain were excised. They were added to 200 μl of a protein lysis buffer (10 mM Tris, 0.5 mM EDTA, 0.25 M sucrose), and proteins were isolated using a grinder. The isolated protein was quantified by the Bradford method (Bio-rad, USA) using bovine serum albumin (BSA, Sigma, USA), and then 25 μg of the protein was separated by 10% sodium dodecyl sulfate-polyacrylamide gel electrophoresis (SDS-PAGE) and transferred to polyvinylidene difluoride (PVDF) membrane (Gendepot, UK). PVDF membranes were blocked in 5% skimmed milk (BD, USA) for 1 hour. After washing with tris-buffered saline and Tween 20 (TBST), they were reacted at 4° C. for 1 day in a solution in which primary antibodies [CD11b (a marker of monocytes), c-Fos (a marker of cell excitability), COX-2 (inflammatory mediator) and GAPDH (glyceraldehyde 3-phosphate dehydrogenase)] were diluted in 3% skimmed milk at a ratio of 1:1,000. Then, they were washed 3 times with TBST for 10 minutes each and reacted with a secondary antibody at room temperature for 1 hour. After the secondary antibody reaction, they were washed in TBST, and then the band was confirmed with the ECL system (Santa Cruz, USA). Identification and quantitative analysis of proteins were analyzed using an imaging device ChemiDoc XRS+ (Bio-Rad).

1-8. Reverse Transcription-Polymerase Chain Reaction (RT-PCR)

In order to confirm the inhibitory effect of bornyl acetate on the expression of inflammatory mediators in an animal model of depression induced by chronic restrained stress, mRNA expression was confirmed using reverse transcription-polymerase chain reaction (RT-PCR). Bornyl acetate (100 mg/kg) was orally administered 1 hour before inducing the restrained stress every day. 14 days later, the mice were anesthetized, and the hippocampus and amygdala of the brain were isolated. The isolated tissue was added to 1 ml of Trizol (Invitrogen, USA), the tissue was ground with a grinder, and the RNA was isolated by centrifugation. To synthesize cDNA, 1 μg of total RNA was reacted in reaction mixture including 0.5 μg of Oligo dT, 0.5 mM dNTP mix, 5×first-strand buffer, RNase free, 5 mM dithiothreitol (DTT) and M-MLV reverse transcriptase at 37° C. for 1 hour. RT-PCR analysis was performed according to the manufacturer's instruction (RT-PCR kit; Roche, Germany). PCR primer sequences are shown in Table 1 below. For PCR amplification, specific oligonucleotide primer pairs were reacted with 1 μl of cDNA and 0.6 U of Econo TaqDNA polymerase in 6 μl of PCR Master Mix (Lucigen, WI, USA). 5-7 μl of the resultant was electrophoresed on a 2% agarose gel, and after staining with ethidium bromide in a trend illuminator, the results were confirmed. The expression level of each gene was normalized with glyceraldehyde 3-phosphate dehydrogenase (GAPDH).

TABLE 1

| Target gene | primer Name | Sequence | Direction | Sequence NO. |
|---|---|---|---|---|
| COX-2 | COX-2_F | CAG TAT CAG AAC CGC ATT GCC | Forward | 1 |
|  | COX-2_R | GAG CAA GTC CGT GTT CAA GGA | Reverse | 2 |

TABLE 1-continued

| Target gene | Name | primer Sequence | Direction | Sequence NO. |
|---|---|---|---|---|
| GAPDH | GAPDH_F | AGG TCA TCC CAG AGC TGA ACG | Forward | 3 |
|  | GAPDH_R | CAC CCT GTT GCT GTA GCC GTA T | Reverse | 4 |
| iNOS | iNOS_F | GGC AAA CCC AAG GTC TAC GTT | Forward | 5 |
|  | iNOS_R | TCG CTC AAG TTC AGC TTG GT | Reverse | 6 |

1-9. Statistic Process

All results were analyzed using the SPSS 21.0 package (SPSS Inc, Chicago, USA), and the experimental results were shown as mean±standard deviation values. Statistical significance was verified after analysis using ANOVA (one-way ANOVA). The post hoc analysis was performed by Tukey post hoc. The significance probability (p-value) was recognized only when $p<0.05$ and $p<0.01$.

Example 1. Antidepressant Efficacy of Bornyl Acetate Through Behavioral Test

In order to confirm the antidepressant effect of bornyl acetate through behavioral tests in an animal model of chronic restrained stress (CRS)-induced stress depression, changes in weight, tail suspension test, forced swimming test, numerical changes in serum stress hormone (corticosterone) level were confirmed.

Figure 1B:
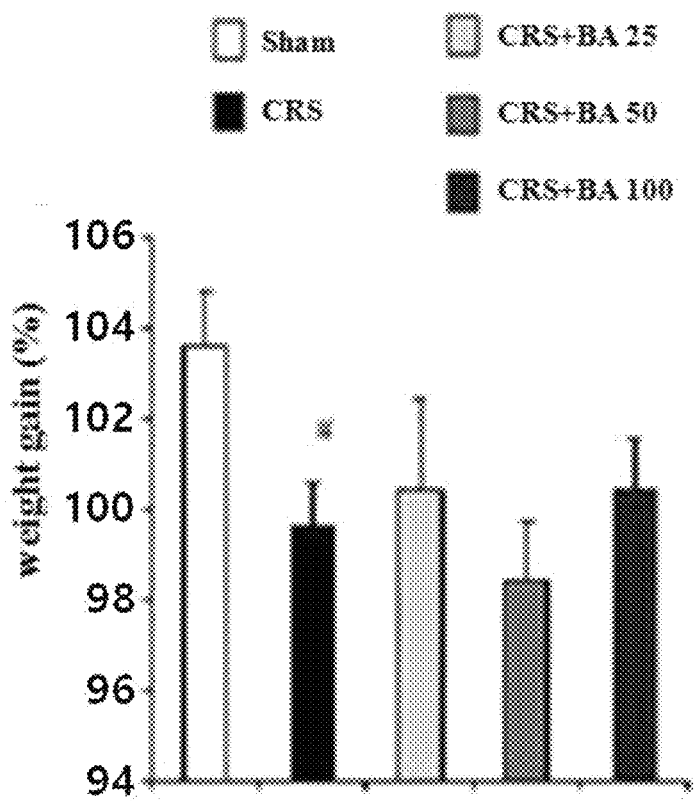
FIG. 1B is a view confirming the weight gain and loss before and after the experiment in an animal model of stress depression induced by chronic restrained stress (CRS).

Specifically, the mice were weighed during or after applying restrained stress for 2 hours per day for 14 days, followed by a tail suspension test and forced swimming test were performed, and serum stress hormone (corticosterone) levels were measured (FIGS. 1A and 1B). As a result, when chronic restrained stress was applied, the weight loss in the CRS group continued to appear and significantly decreased compared to the Sham group on the 14th day, but the CRS+BA group had no significant increase or decrease.

Figure 1C:
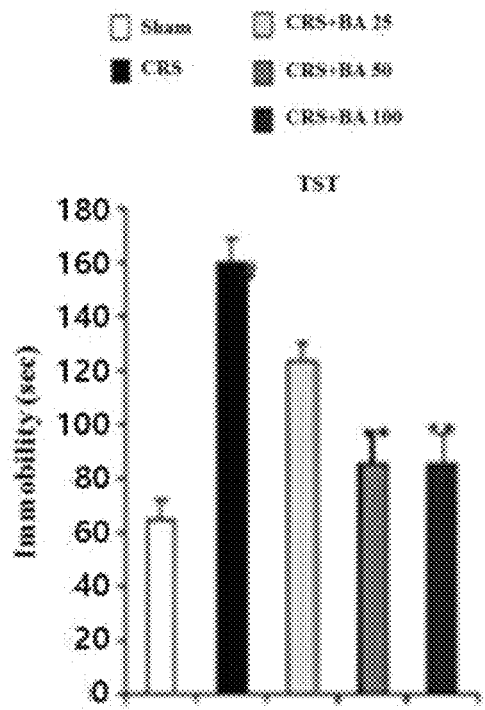
FIG. 1C is a view confirming the tail suspension test in an animal model of stress depression induced by chronic restrained stress (CRS).
Figure 1D:
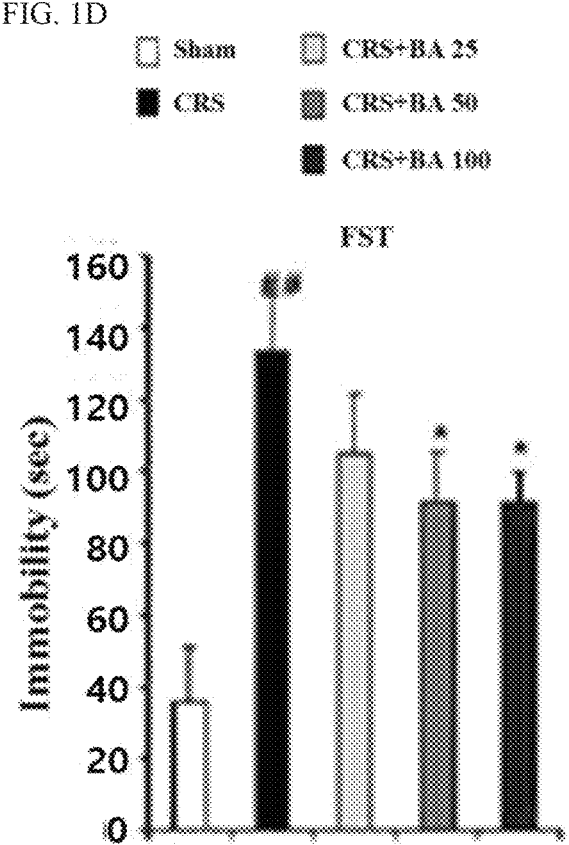
FIG. 1D is a diagram confirming the forced swimming test in an animal model of stress depression induced by chronic restrained stress (CRS).
Figure 1E:
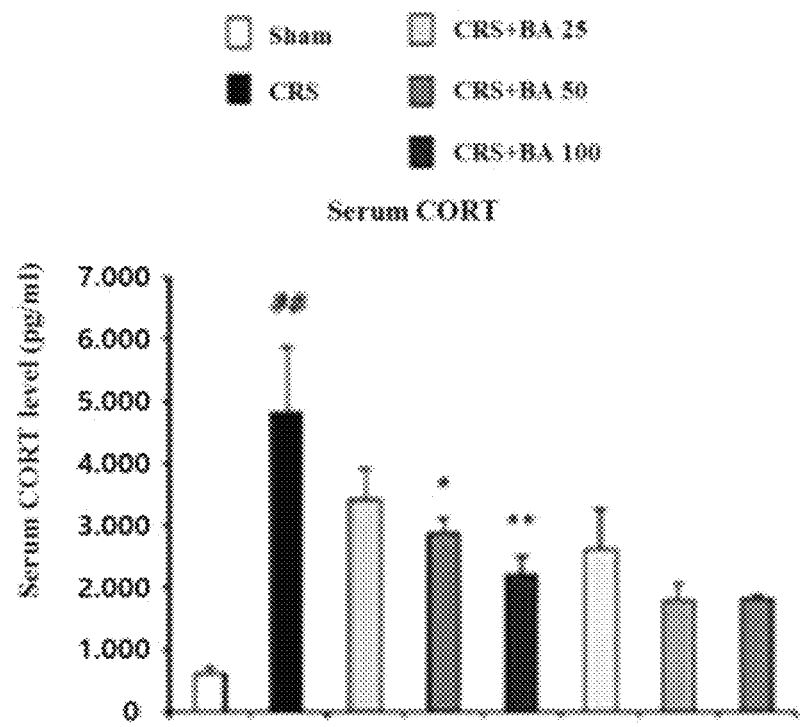
FIG. 1E is a diagram confirming the serum stress hormone (corticosteroid) level in an animal model of stress depression induced by chronic restrained stress (CRS).

Further, in the case of the tail suspension test and the forced swimming test, the time of immobility in the CRS group (160 seconds and 133.6 seconds) was significantly increased compared to the time of immobility in the Sham group (64.7 seconds and 35.7 seconds). However, this increase was significantly decreased in the CRS+BA group (91.4 seconds and 85.2 seconds) (FIGS. 1C and 1D). The level of stress hormone (corticosterone) in serum was significantly increased in the CRS group (4822.3 pg/ml) compared to the Sham group, and the level was significantly decreased in the CRS+BA group (2869.8 pg/ml for 50 mg/kg and 2202.5 pg/ml for 100 mg/kg) (FIG. 1E).

Example 2. Inhibitory Effect of Bornyl Acetate on Activation of Microglia

Western blot analysis and immunohistochemistry staining were performed on the brain (hippocampus and amygdala) of an animal model of chronic restrained stress (CRS)-induced stress depression to confirm the activation degree of microglia, thereby verifying the inhibitory effect of bornyl acetate on the activation of microglia (immune cells of the nervous system) in an animal model of chronic stress depression.

Specifically, the hippocampus and amygdala of the mouse brain were collected. Western blot was performed for CD11b, a monocyte marker, and immunostaining was performed for Iba-1, a microglia marker.

Figure 2A:
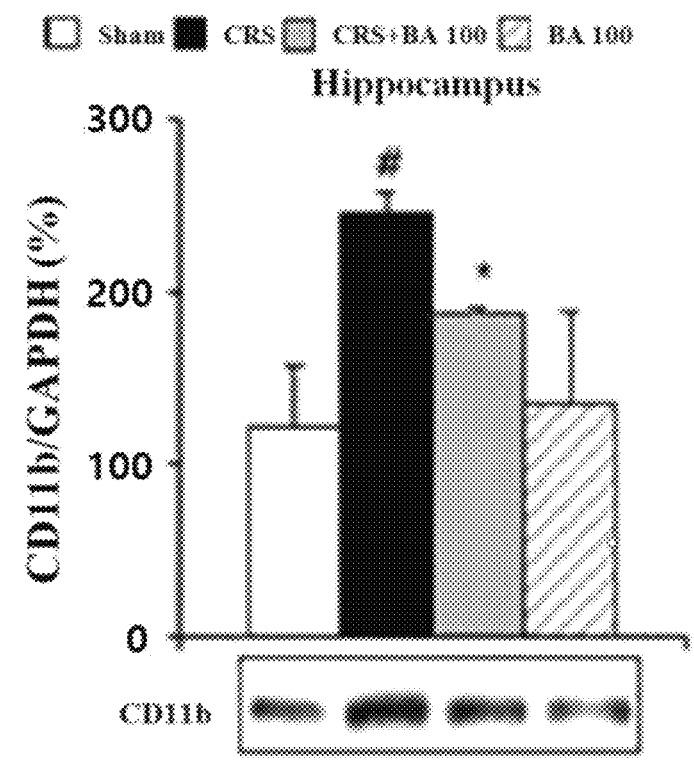
FIG. 2A is a view confirming the Western blot analysis and quantification of CD11b protein in the brain (hippocampus) of an animal model of stress depression induced by chronic restrained stress (CRS).
Figure 2B:
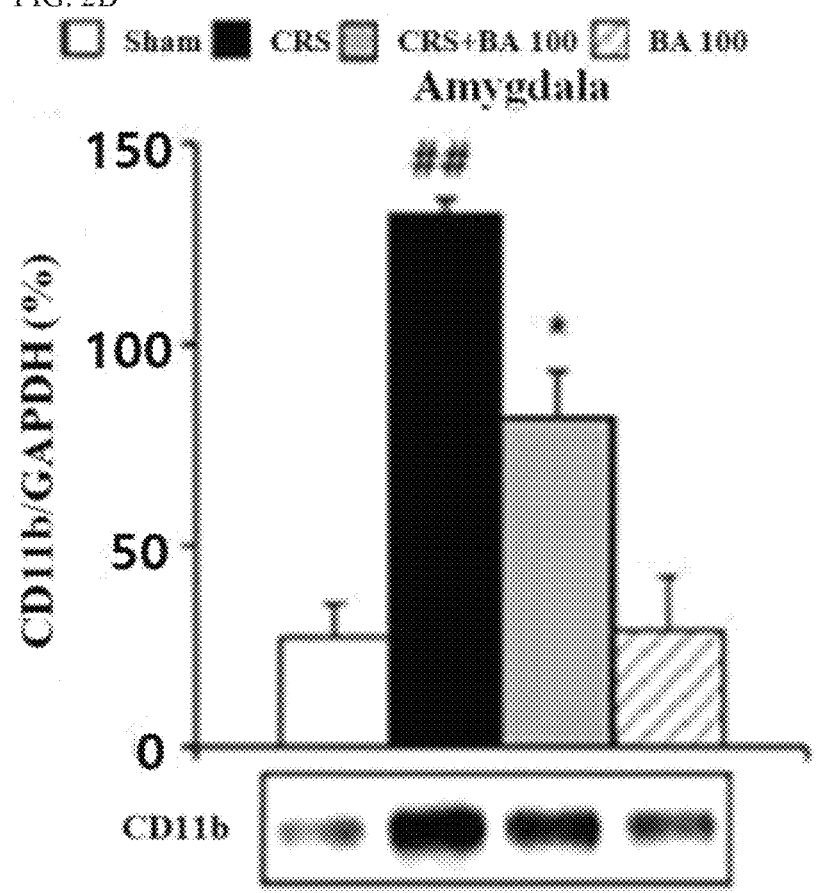
FIG. 2B is a view confirming Western blot analysis and quantification of CD11b protein in the brain (amygdala) of an animal model of stress depression induced by chronic restrained stress (CRS).
Figure 2C:
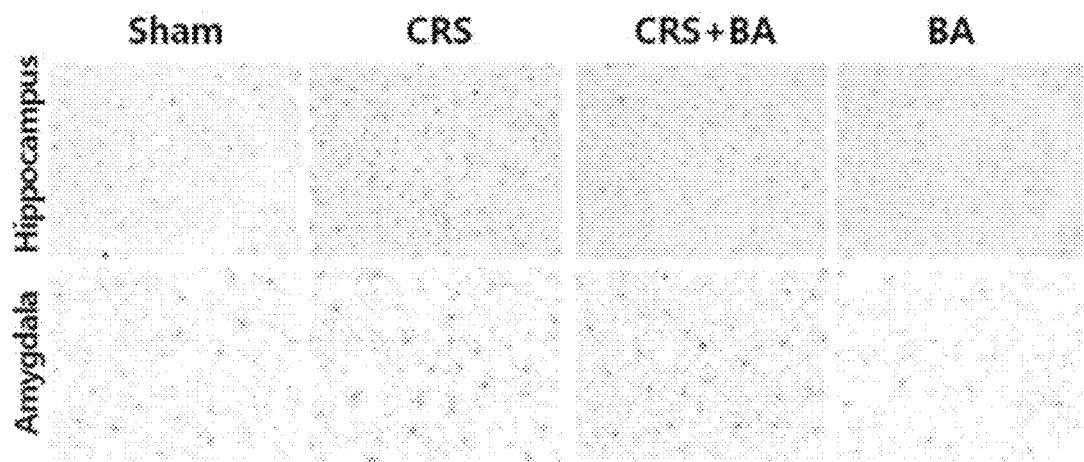
FIG. 2C is a view showing the immunohistochemical staining results for Iba-1 in the brain (hippocampus and amygdala) of an animal model of stress depression induced by chronic restrained stress (CRS).

As a result, the expression of CD11b protein in the hippocampus and amygdala of the CRS group was significantly increased compared to the Sham group, and this increase was significantly inhibited in the CRS+BA group (FIGS. 2A and 2B). These results were consistent with the activation degree of microglia immunostained by Iba-1 (FIG. 2C).

Example 3. Confirmation of Responsiveness of Bornyl Acetate to Cell/Neural Stimulation Western blot analysis and immunohistochemistry staining were performed for the brain (hippocampus and amygdala) of an animal model of chronic restrained stress (CRS)-induced stress depression to confirm the activation level of c-Fos. The analysis verified the inhibitory effect of bornyl acetate on the degree of nerve excitability in an animal model of chronic stress depression.

Specifically, hippocampus and amygdala were collected, and Western blot for c-Fos, a marker of cell excitability, and immunostaining for c-Fos were performed.

Figure 3A:
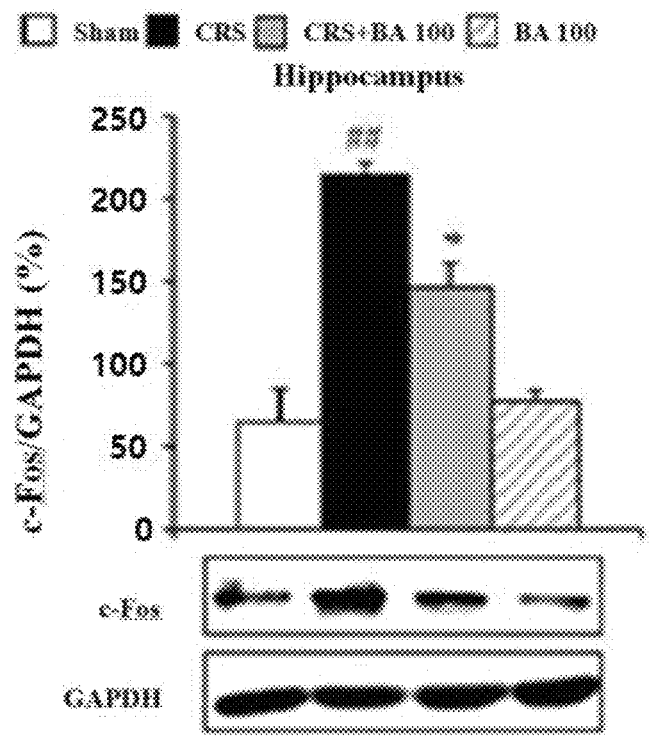
FIG. 3A is a view confirming Western blot analysis and quantification of c-Fos protein in the brain (hippocampus) of an animal model of stress depression induced by chronic restrained stress (CRS).
Figure 3B:
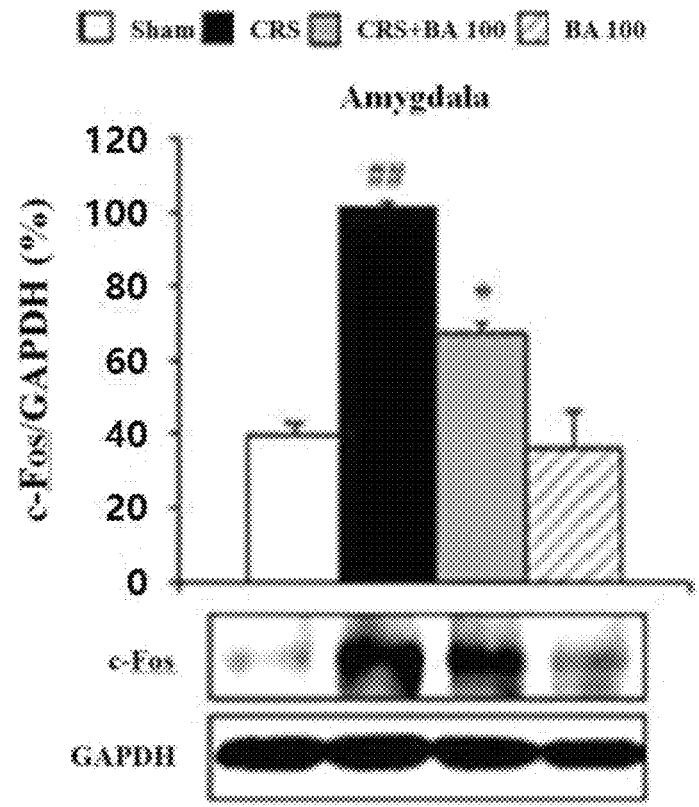
FIG. 3B is a view confirming Western blot analysis and quantification of c-Fos protein in the brain (amygdala) of an animal model of stress depression induced by chronic restrained stress (CRS).
Figure 3C:
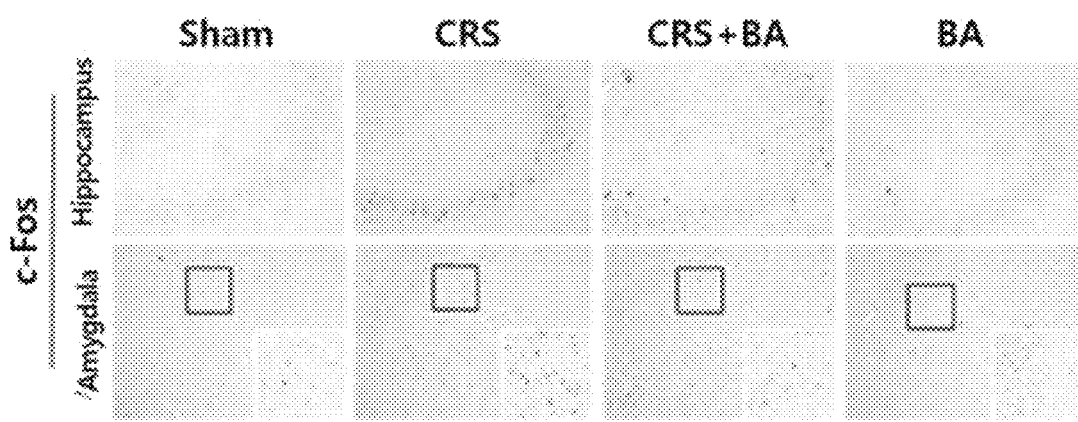
FIG. 3C is a view showing the immunohistochemical staining results for c-Fos in the brain (hippocampus and amygdala) of an animal model of stress depression induced by chronic restrained stress (CRS).
Figure 4A:
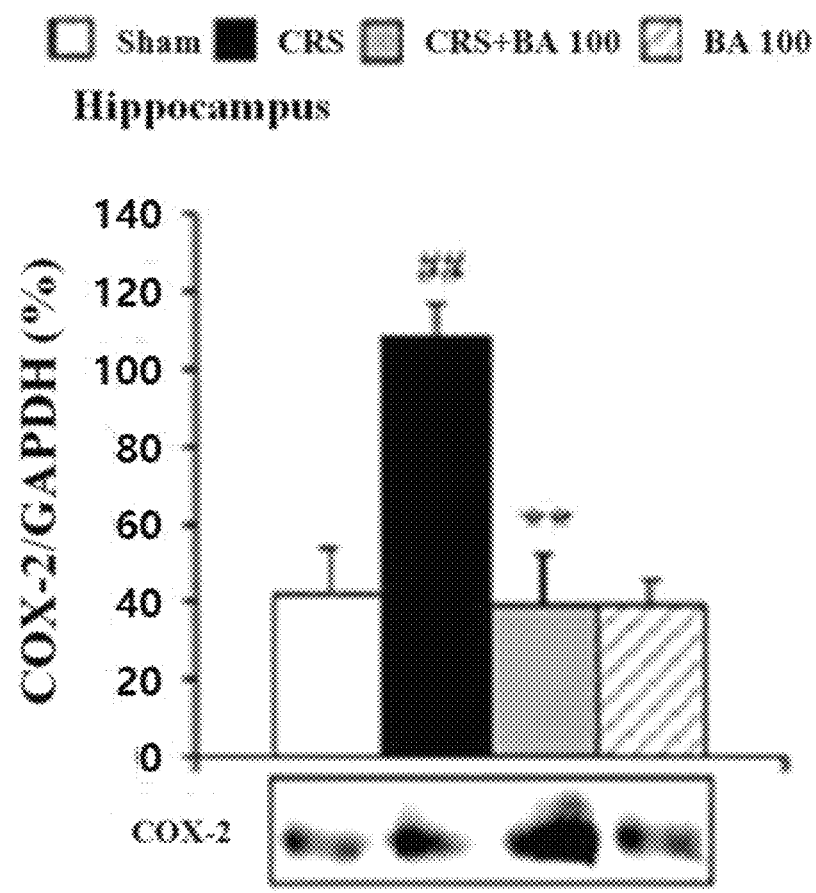
FIG. 4A is a view confirming a Western blot analysis and quantification of COX-2 protein in the brain (hippocampus) of an animal model of stress depression induced by chronic restrained stress (CRS).
Figure 4B:
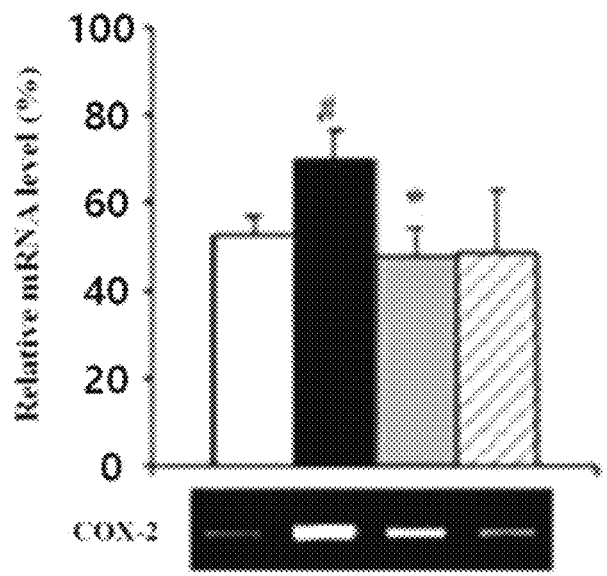
FIG. 4B is a view showing RT-PCR analysis and quantification of COX-2 mRNA in the brain (hippocampus) of an animal model of stress depression induced by chronic restrained stress (CRS).
Figure 4C:
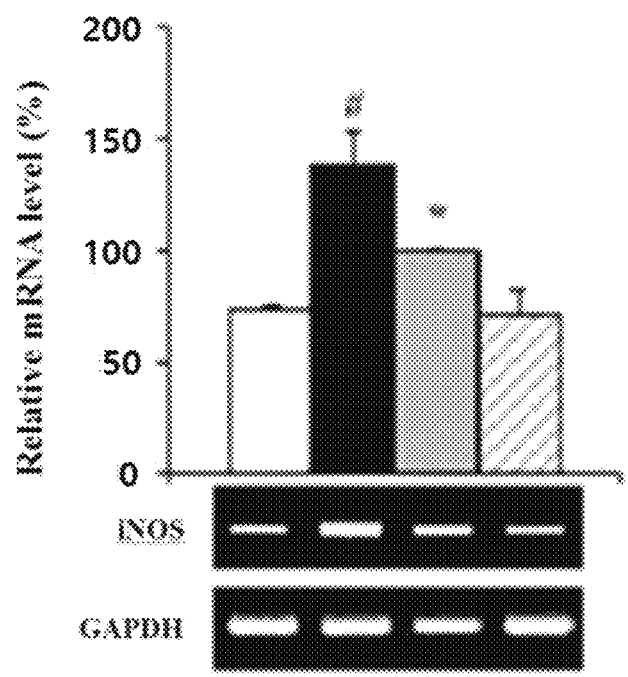
FIG. 4C is a view showing RT-PCR analysis and quantification of iNOS mRNA in the brain (hippocampus) of an animal model of stress depression induced by chronic restrained stress (CRS).
Figure 4D:
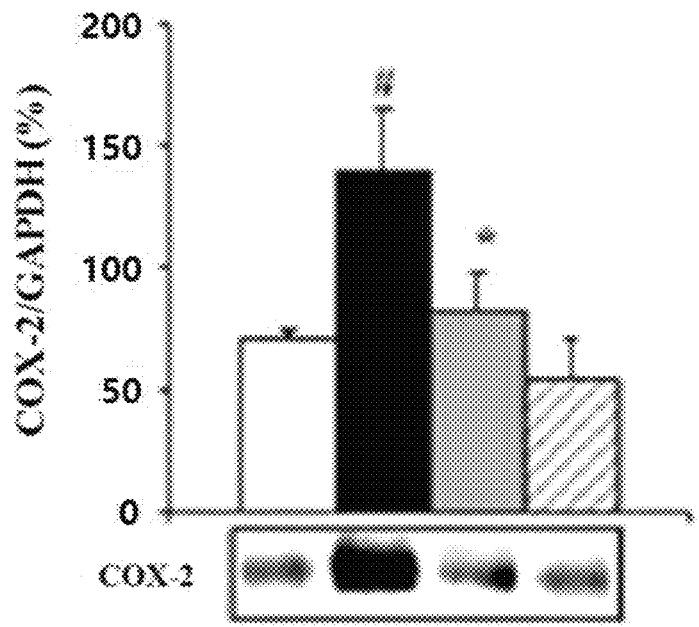
FIG. 4D is a view showing Western blot analysis and quantification of COX-2 protein in the brain (amygdala) of an animal model of stress depression induced by chronic restrained stress (CRS).
Figure 4E:
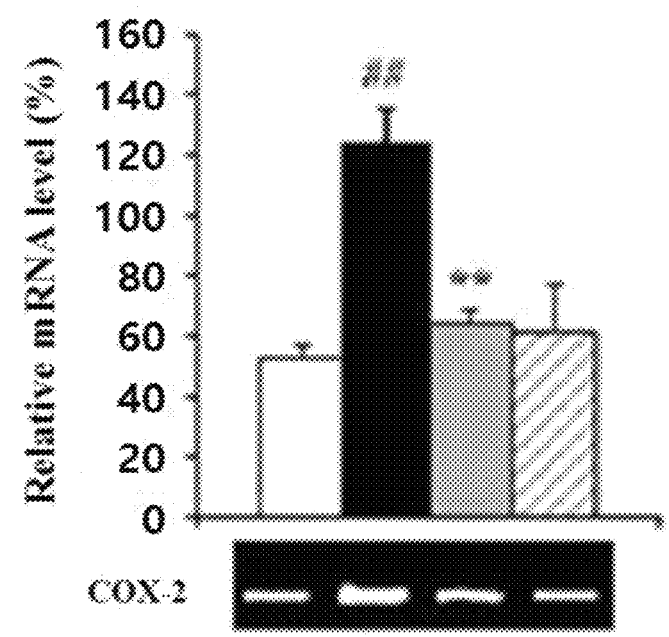
FIG. 4E is a view showing RT-PCR analysis and quantification of COX-2 mRNA in the brain (amygdala) of an animal model of stress depression induced by chronic restrained stress (CRS).
Figure 4F:
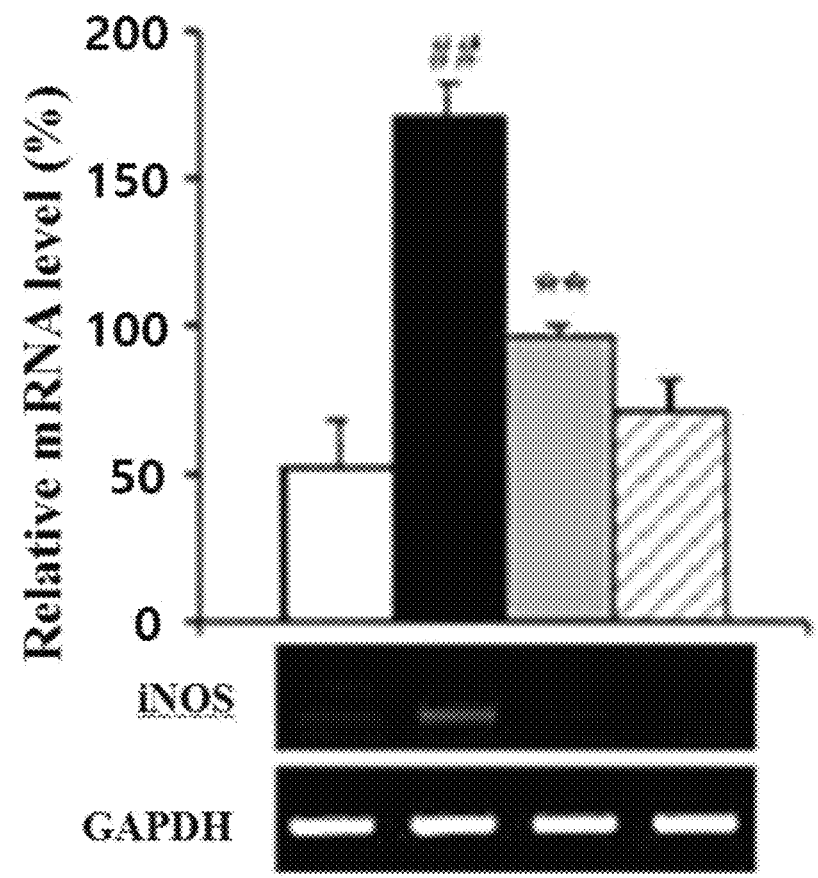
FIG. 4F is a view showing RT-PCR analysis and quantification of iNOS mRNA in the brain (amygdala) of an animal model of stress depression induced by chronic restrained stress (CRS).

As a result, the protein expression of c-Fos in the hippocampus and amygdala was significantly increased compared to the Sham group, and this increase was significantly inhibited in the CRS+BA group (FIGS. 3A to 3B). These results were consistent with the distribution of cells immunostained by c-Fos (FIG. 3C).

Example 4. Confirmation of Inhibition of Inflammatory Mediator by Bornyl Acetate Western blot and RT-PCR analysis were performed in the brain (hippocampus and amygdala) of an animal model of chronic restrained stress (CRS)-induced stress depression to exam and quantify the activation level of inflammatory mediators, thereby verifying the modulating effect of bornyl acetate on the inflammatory response in the brain.

Specifically, hippocampus and amygdala were collected, and Western blot or RT-PCR analysis was performed for COX-2 and iNOS, which are inflammatory mediators.

As a result, it was confirmed that protein and mRNA expression of COX-2 and mRNA expression of iNOS in the hippocampus and amygdala were significantly increased compared to the Sham group, and this increase was significantly inhibited in the CRS+BA group (FIGS. 4A to 4F).

The above series of results indicate that when used as an active ingredient, bornyl acetate or a pharmaceutically acceptable salt thereof according to the present invention exhibits the effects of alleviating behavioral scales in an animal model by changes in weight, tail suspension test, forced swimming test and numerical changes in serum stress hormone (corticosterone) level. Further, it inhibits the activation of microglia and the generation of inflammatory factors (COX-2 and iNOS), and lowers the degree of nerve excitability for responsiveness to cell-neural stimuli. Thus, bornyl acetate or a pharmaceutically acceptable salt thereof is found to have excellent stress modulating potential and to be useful for the prevention and treatment of stress-related diseases, especially, depression.

The invention claimed is:

1. A method for treating depression, the method comprising administering a pharmaceutically effective amount of a composition comprising bornyl acetate or a pharmaceutically acceptable salt thereof as an active ingredient to a subject in need thereof.

2. The method of claim 1, wherein the bornyl acetate is represented by the following formula 1

[Formula 1]

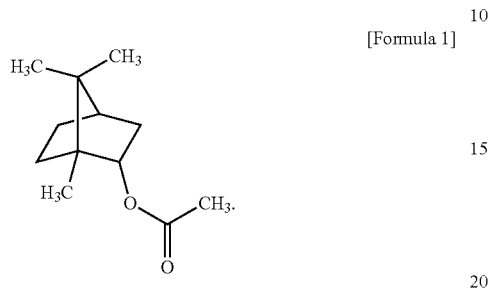

3. The method of claim 1, wherein the composition inhibits expressions of COX-2 and iNOS as inflammatory factors.

4. The method of claim 1, wherein the composition inhibits activation of microglia.

5. The method of claim 1, wherein the composition inhibits responsiveness to cell-neural stimulation.

* * * * *

```
                              SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: COX-2_F primer

<400> SEQUENCE: 1
cagtatcaga accgcattgc c                                                   21

<210> SEQ ID NO 2
<211> LENGTH: 21
<212> TYPE: DNA
<213> ORGANISM: Artificial Sequence
<220> FEATURE:
<223> OTHER INFORMATION: COX-2_R primer

<400> SEQUENCE: 2
gagcaagtcc gtgttcaagg a                                                   21

<210> SEQ ID NO 3
<211> LENGTH: 21
<212> TYPE: DNA
<213> ORGANISM: Artificial Sequence
<220> FEATURE:
<223> OTHER INFORMATION: GAPDH_F primer

<400> SEQUENCE: 3
aggtcatccc agagctgaac g                                                   21

<210> SEQ ID NO 4
<211> LENGTH: 22
<212> TYPE: DNA
<213> ORGANISM: Artificial Sequence
<220> FEATURE:
<223> OTHER INFORMATION: GAPDH_R primer

<400> SEQUENCE: 4
caccctgttg ctgtagccgt at                                                  22

<210> SEQ ID NO 5
<211> LENGTH: 21
<212> TYPE: DNA
<213> ORGANISM: Artificial Sequence
<220> FEATURE:
<223> OTHER INFORMATION: iNOS_F primer

<400> SEQUENCE: 5
ggcaaaccca aggtctacgt t                                                   21

<210> SEQ ID NO 6
<211> LENGTH: 20
<212> TYPE: DNA
<213> ORGANISM: Artificial Sequence
<220> FEATURE:
<223> OTHER INFORMATION: iNOS_R primer

<400> SEQUENCE: 6
tcgctcaagt tcagcttggt                                                     20
```